United States Patent
Milleville et al.

(10) Patent No.: US 7,805,976 B2
(45) Date of Patent: Oct. 5, 2010

(54) METHOD FOR CHECKING SURFACE CONDITION AFTER CLEANING

(75) Inventors: Timothy A. Milleville, Portland, CT (US); Beth K. Abriles, Madison, CT (US); Edward R. Szela, West Springfield, MA (US)

(73) Assignee: United Technologies Corporation, Hartford, CT (US)

( * ) Notice: Subject to any disclaimer, the term of this patent is extended or adjusted under 35 U.S.C. 154(b) by 636 days.

(21) Appl. No.: 11/732,324

(22) Filed: Apr. 2, 2007

(65) Prior Publication Data
US 2008/0236244 A1 Oct. 2, 2008

(51) Int. Cl.
*G01N 3/56* (2006.01)
(52) U.S. Cl. .......................................... 73/7
(58) Field of Classification Search .................. 73/7
See application file for complete search history.

(56) References Cited

U.S. PATENT DOCUMENTS

| | | | |
|---|---|---|---|
| 5,375,451 A * | 12/1994 | Sandstrom | 73/7 |
| 6,336,983 B1 * | 1/2002 | Fawley | 156/94 |
| 6,561,883 B1 * | 5/2003 | Kondo et al. | 451/63 |
| 7,013,705 B2 * | 3/2006 | Wortmann et al. | 73/7 |
| 7,059,665 B2 * | 6/2006 | Murai et al. | 296/181.2 |
| 7,422,678 B2 * | 9/2008 | Kendig et al. | 205/775.5 |

FOREIGN PATENT DOCUMENTS

| | | |
|---|---|---|
| EP | 1685923 A1 | 8/2006 |
| JP | 03013861 A1 | 1/1991 |
| JP | 03081638 A | 4/1991 |
| JP | 06074951 A | 3/1994 |
| SU | 1138692 A | 2/1985 |

OTHER PUBLICATIONS

European Search Report, dated Jul. 10, 2008.

* cited by examiner

*Primary Examiner*—Hezron Williams
*Assistant Examiner*—Rodney T Frank
(74) *Attorney, Agent, or Firm*—Bachman & LaPointe, P.C.

(57) ABSTRACT

Methods for inspecting gas turbine component parts for possible distress after hydrogen fluoride cleaning are disclosed. The methods selectively remove a small amount of material for IGA inspection and restore the material using the same procedures as when the parts were manufactured.

9 Claims, 3 Drawing Sheets

METHOD FOR CHECKING SURFACE CONDITION AFTER CLEANING

BACKGROUND OF THE INVENTION

The invention relates generally to the field of component part inspection. More specifically, the invention relates to methods for inspecting gas turbine component parts after hydrogen fluoride cleaning.

Today's high strength braze repairs require very aggressive cleaning techniques in order to provide the level of cleanliness required to achieve optimum strength. These cleaning techniques do not discriminate between oxidation and contamination, and the elements that are designed to occupy the space between grain boundaries in a given alloy. Removal of these native elements from the grain boundaries is known as intergranular attack (IGA). Intergranular attack, also known as intergranular corrosion (IGC), is a form of corrosion where the boundaries of crystallites of the material are more susceptible to corrosion. This attack is common in some stainless steels and nickel alloys.

Fluoride cleaning systems are used to remove unwanted oxides from surfaces and service induced cracks of turbine engine components, such as turbine blade airfoils, formed from nickel base superalloys prior to repairing the components. Hydrogen fluoride gas used in the cleaning treatment both depletes and intergranularly attacks the component surfaces and the exposed cracks, removing essential elements that form grain boundary carbides (i.e. grain boundary strengthening phases), leaving for some specific applications a desirable gamma layer on the surface and along the cracks which allow for capillary action during brazing. This depletion layer on the base superalloy is typically between about 0.0004 and 0.0012 inch deep. Presently acceptable levels of intergranular attack can be as high as about 0.011 inch deep in some alloys and some types of turbine airfoils.

Hydrogen fluoride cleaning used to clean parts results in IGA. Those components that can tolerate depletion and intergranular attack from the fluoride cleaning can be repaired and returned to service. If IGA is too deep, it can impact the integrity of the part by providing crack initiation sites.

Current methods for monitoring the extent of IGA involve processing coupons with parts to be cleaned. Coupons are cast pieces or pieces cut from a scrap component made of the same material as the cleaned parts. The coupons are sectioned to evaluate the level of IGA. Sample pieces may also be removed from the cleaned parts. The area(s) where the removed sample pieces were removed may have to be restored by puddle welding if the area cannot tolerate the missing material. The least attractive method is sacrificing a part to evaluate the level of IGA.

The coupon method has the drawback that the coupon has not experienced engine operation and may not have experienced the affects of any previous coating applications performed when assembled, or any coating removal prior to repair. Removing sample pieces may require welding to restore the part back to its original geometry. Further, welding of these superalloys is often difficult, resulting in heat affected zone cracking which results in reduced strength. Sacrificing one part examines only that part, not a number of parts.

Monitoring IGA is an important quality issue. An improved method for broad applications for repair procedures is desired.

SUMMARY OF THE INVENTION

Although there are various methods for monitoring the extent of intergranular attack, such methods are not completely satisfactory. The inventors have discovered that it would be desirable to have methods for inspecting gas turbine component parts for possible corrosive distress after hydrogen fluoride cleaning. The method selectively removes a small amount of material for determining whether grain boundaries of the material are depleted and restores the material using the same procedures as when the parts were manufactured.

Embodiments of the invention provide methods for determining corrosion in a component part. These methods comprise choosing an area of the component part for examination, removing a predetermined amount of material from the surface of the area to create a new surface, polishing the new surface to a predetermined depth to create a polished surface, determining corrosion in the component part, and restoring the polished surface back to original dimensions.

Other embodiments of the invention provide methods for inspecting gas turbine component parts for distress. These methods comprise selectively removing a small amount of material from the component part, determining whether grain boundaries are depleted where the material was removed, and restoring the removed material using the same procedures as when the component part was manufactured.

The details of one or more embodiments of the invention are set forth in the accompanying drawings and the description below. Other features, objects, and advantages of the invention will be apparent from the description and drawings, and from the claims.

DETAILED DESCRIPTION

Embodiments of the invention will be described with reference to the accompanying drawing figures wherein like numbers represent like elements throughout. Further, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

Component part surfaces to be cleaned may be subjected to a fluoride cleaning treatment which uses hydrogen fluoride (HF) gas. The fluoride cleaning treatment may be any suitable fluoride cleaning treatment known in the art.

Nickel base superalloys, when subjected to a fluoride cleaning treatment using hydrogen fluoride gas, exhibit a general depletion layer about 0.0004 to 0.0012 inch deep, a localized depletion layer about 0.004 to 0.009 inch deep, and a maximum intergranular attack about 0.004 to 0.008 inch deep, for cases in which intergranular and/or interdendritic boundaries are encountered.

Component parts, such as vanes and blades used in gas turbine engines, may suffer structural distress due to the hydrogen fluoride gas when cleaned. The cleaning process may attack critical areas on the component part and contribute to, or exacerbate, IGA. For component parts that have undergone HF cleaning, the invention provides methods for inspecting each part for any IGA that may have occurred.

Figure 1:
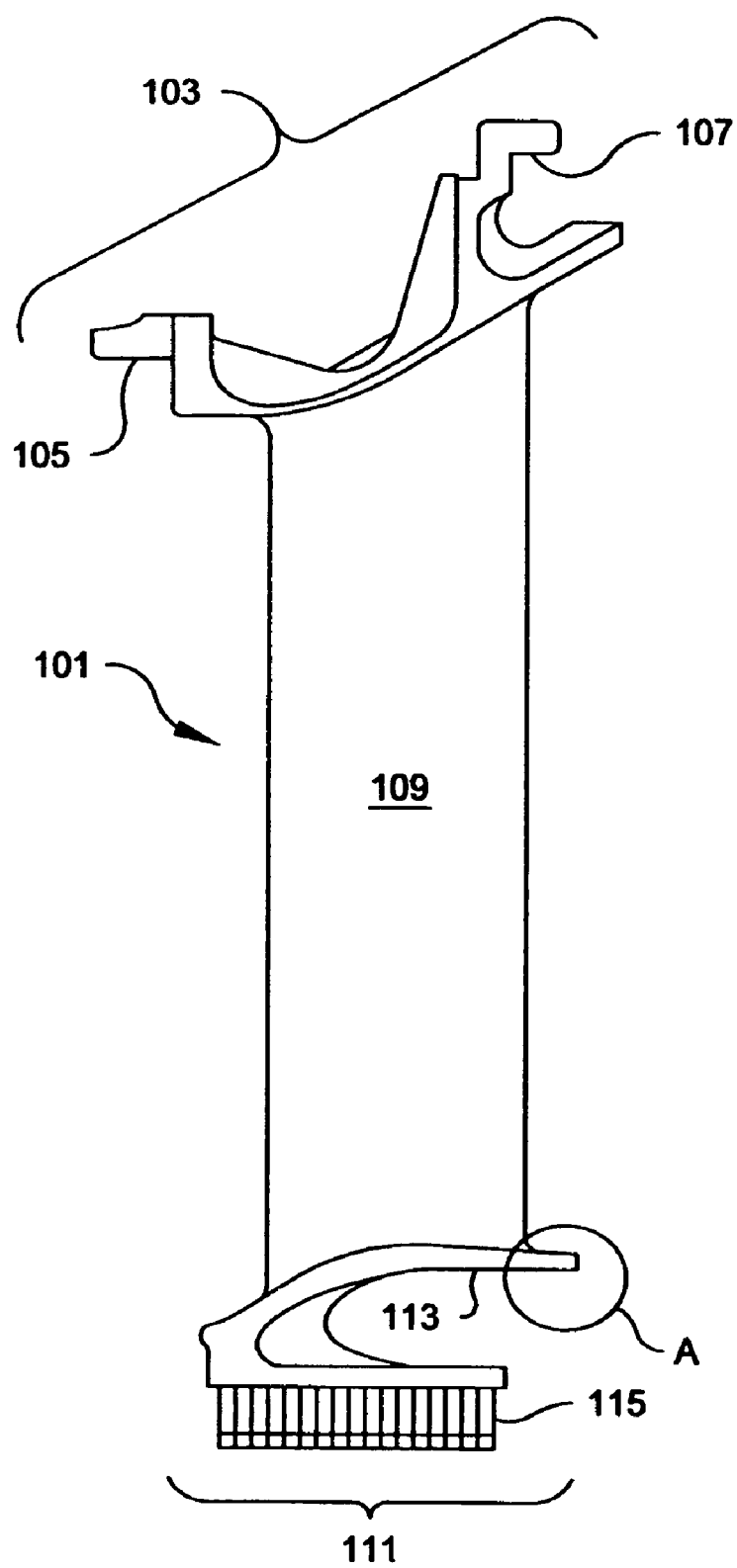
FIG. 1 is an exemplary gas turbine vane showing a post cleaning inspection point.
Figure 3:
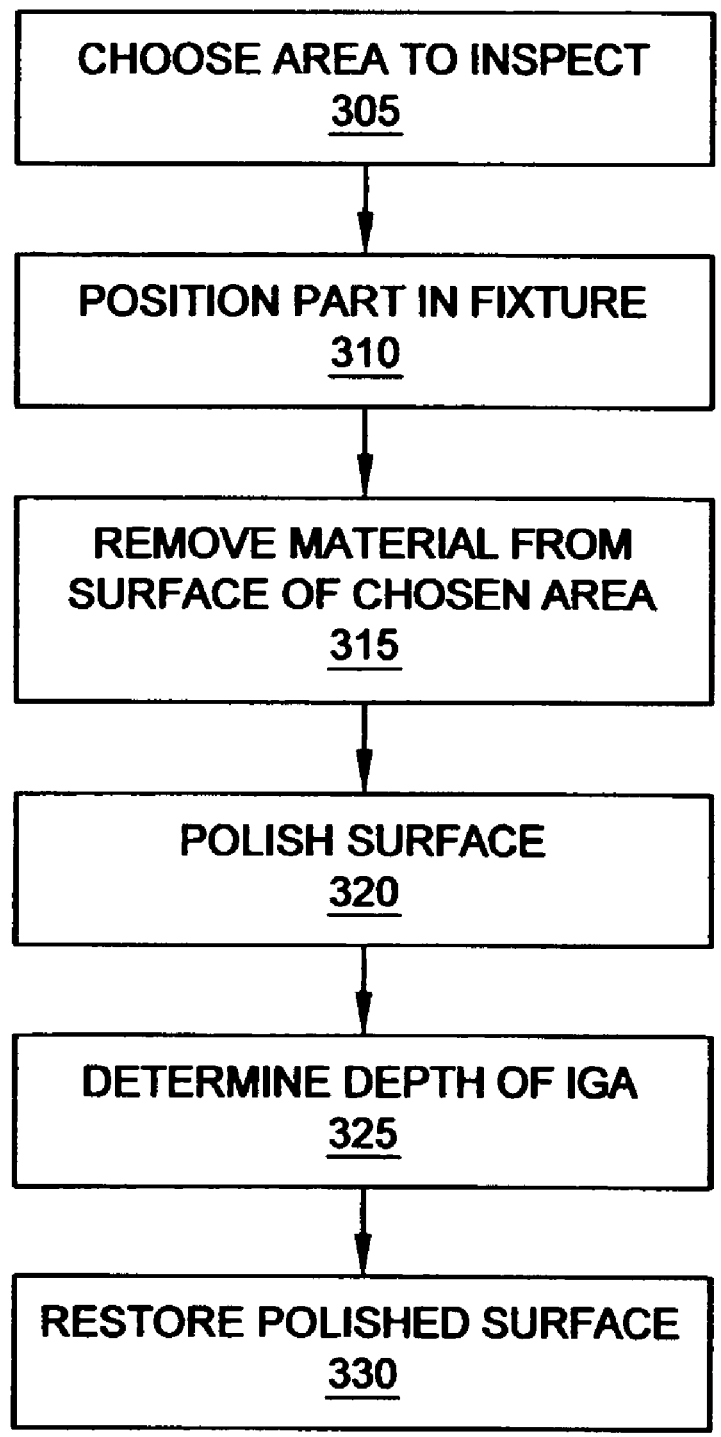
FIG. 3 is a block diagram of an exemplary inspection method according to the invention.

Shown in FIG. 1 is an illustration of a turbine vane 101 that has undergone HF cleaning. Areas of the turbine vane 101 include an outer platform 103 that includes front 105 and rear 107 hook attachments, an airfoil section 109, and an inner platform 111 that includes a rear inner platform edge 113 and a honeycomb seal 115. Shown in FIG. 3 is an exemplary, non-limiting method of the invention. The method examines an area that is typically the most vulnerable and susceptible to IGA. An area, A, determined to be susceptible may be chosen for inspection (step 305). In embodiments, the exemplary area, A, of the rear inner platform edge 113 is chosen due to its gas path and non-gas path exposure, accessibility, and ease of repair after performing the inspection method. The surface chosen for examination may be a marginally loaded edge, or surface, such that performing the method does not impact the structural integrity of the component part. The part 101 may be put in a fixture for positioning and to provide an examination surface reference (step 310).

Figure 2:
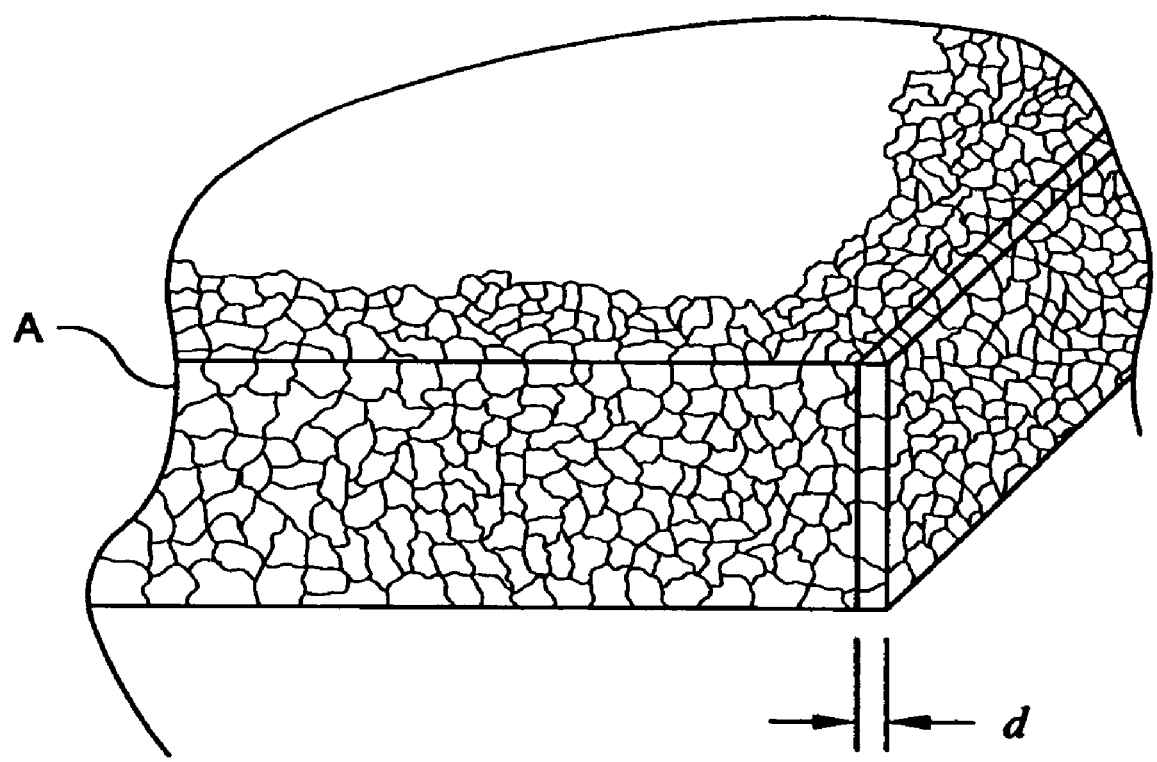
FIG. 2 is the inspection point from FIG. 1 showing intergranular attack affecting all cleaned surfaces.

Material may then be removed from the surface of the chosen area (step 315) to a predetermined depth d as shown in FIG. 2 (in embodiments, about 0.010 to 0.020 inch deep) using a series of abrasive papers that may be comprised of SiC, aluminum oxide, or others. Coarse to fine mesh abrasives may also be used in series to achieve a final polished surface finish.

Thereafter, the surface of the chosen area may be polished to a mirror-like finish (step 320). Polishing may comprise removing about 10 to 15 microns more material from the surface of the chosen area to remove a region that may be affected by IGA.

The depth of the IGA may then be determined (step 325) by evaluating the microstructure of the polished surface. The microstructure evaluation may involve using a replication material. One embodiment uses an acetate replica, but other replication materials or methods may also be used. An acetate replica is typically prepared by cutting a sheet of acetate to an appropriate size for the replica and placing one or two drops of acetone on the surface to be replicated. Bioden acetate film may be used for replica preparation, and acetone or methyl acetate may be used as the solvent. The acetate may have a foil backing to allow viewing with an optical microscope. The acetate is placed on the surface to be replicated and is softened by the acetone. Pressure may be applied to the acetate after the solvent has evaporated to ensure that the acetate molds to the surface being replicated. A predetermined amount of time, usually about 10 minutes, is allowed for the acetate to capture a "hills and valleys" impression before removing the replica from the sample surface.

Usually, a first replica will clean the surface. The first replica may be saved for analysis as well since it may contain corrosion products. A second replica is typically prepared for analysis. Due to IGA size, electron microscopy may not be required for evaluation. For evaluation of finer microstructure features such as gamma prime sizes, electron microscopy may be used.

In embodiments, the replica may be examined using an optical microscope to examine the hills and valleys. IGA may be determined by measuring the differences between the highest peaks and lowest valleys to form a metric for comparison. The measured data may then be compared with acceptable limits, which may be published in manufacturers' technical data such as internal engineering notices or technical work packages. An acceptable IGA depth is limited by engine structural experience, mechanical property testing and overall structure calculation (maximum operating stress level and fatigue life requirements).

The material removed by polishing may then be restored using diffusion brazing (i.e., TurboFIX®) or welding (step 330). If necessary, the restored material may then be machined to return the component part back to the original part dimensions.

This invention eliminates the need to sacrifice parts, or weld restore large regions (greater than about 0.5×0.5 inch) removed by prior art IGA examination methods. The invention allows each component part, if necessary, to be examined for IGA in a manner such that material removed for inspection may be restored using the same braze procedures the parts were exposed to during manufacture or repair.

One or more embodiments of the present invention have been described. Nevertheless, it will be understood that various modifications may be made without departing from the spirit and scope of the invention. Accordingly, other embodiments are within the scope of the following claims.

What is claimed is:

1. A method for determining corrosion in a component part comprising:
    choosing an area of the component part for examination;
    removing a predetermined amount of material from the surface of said area to create a new surface;
    polishing said new surface to a predetermined depth to create a polished surface;
    determining corrosion in the component part;
    said corrosion determining step comprising evaluating corrosion by examining said polished surface; and
    restoring said polished surface back to original dimensions.

2. The method according to claim 1 wherein said removing step comprises removing material from said surface to a depth of about 0.010 to 0.020 inch.

3. The method according to claim 1 wherein said polishing step comprises polishing said new surface to remove additional material from said new surface to a depth of about 10 to 15 microns.

4. The method according to claim 1 wherein examining said polished surface comprises creating a replica of said polished surface microstructure.

5. The method according to claim 4 further comprising examining microstructure peaks and valleys of said replica to create a metric of corrosive effects.

6. The method according to claim 5 further comprising comparing said metric with empirical results to determine if corrosion exists in the component part.

7. The method according to claim 6 wherein said restoring step comprises applying additional material compatible with said component part to said polished surface.

8. The method according to claim 7 further comprising machining said additional material back to said original dimensions.

9. The method according to claim 8 where in the component part is a turbine vane.

* * * * *